United States Patent [19]

Walker

[11] Patent Number: 4,561,876
[45] Date of Patent: Dec. 31, 1985

[54] HALOALKYLCARBONYLAMINO-1,3-DIOXANE HERBICIDE ANTIDOTES

[75] Inventor: Francis H. Walker, Mill Valley, Calif.

[73] Assignee: Stauffer Chemical Co., Westport, Conn.

[21] Appl. No.: 271,899

[22] Filed: Jun. 16, 1981

Related U.S. Application Data

[60] Continuation-in-part of Ser. No. 144,703, Apr. 28, 1980, which is a division of Ser. No. 23,222, Mar. 23, 1979, abandoned.

[51] Int. Cl.$^4$ .................. A01N 43/00; C07D 319/06
[52] U.S. Cl. ............................................. 71/88; 549/371
[58] Field of Search .................. 549/449, 452, 371; 71/88

[56] References Cited

U.S. PATENT DOCUMENTS

| | | | |
|---|---|---|---|
| 2,568,555 | 9/1951 | Moore | 549/371 |
| 4,116,670 | 9/1978 | Stach et al. | 71/88 |
| 4,221,584 | 9/1980 | Ziman | 548/198 |
| 4,276,078 | 6/1981 | Pallos et al. | 71/118 |
| 4,294,764 | 10/1981 | Rinehart | 549/452 |
| 4,336,058 | 6/1982 | Felix | 71/88 |
| 4,396,414 | 8/1983 | Buren | 71/88 |
| 4,512,796 | 4/1985 | Walker | 71/88 |

FOREIGN PATENT DOCUMENTS 0068709 1/1983 European Pat. Off. ........... 71/88

Primary Examiner—Ethel G. Love
Attorney, Agent, or Firm—Harry A. Pacini

[57] ABSTRACT

Herbicide antidote compounds having the formula:

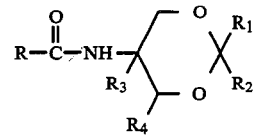

in which
R is haloalkyl wherein halo is chlorine, bromine or iodine and the alkyl group has 1–4 carbon atoms, inclusive;
$R_1$ is selected from the group consisting of hydrogen; lower alkyl having 1–4 carbon atoms, inclusive; alkenyl having 2–4 carbon atoms, inclusive; and phenyl;
$R_2$ is selected from the group consisting of hydrogen and lower alkyl having 1–4 carbon atoms, inclusive;
$R_3$ is selected from the group consisting of hydrogen and lower alkyl having 1–4 carbon atoms, inclusive;
$R_4$ is selected from the group consisting of hydrogen and a nitro group; and
either $R_3$ is hydrogen or $R_4$ is hydrogen.

41 Claims, No Drawings

HALOALKYLCARBONYLAMINO-1,3-DIOXANE HERBICIDE ANTIDOTES

CROSS REFERENCE TO RELATED APPLICATIONS

This is a continuation-in-part of currently pending U.S. patent application Ser. No. 144,703, filed Apr. 28, 1980, which is a divisional of U.S. patent application Ser. No. 023,222, filed Mar. 23, 1979, now abandoned.

FIELD OF THE INVENTION

This invention relates to herbicide antidotes, and, more particularly, to certain haloalkylcarbonylamino-1,3-dioxanes which are useful as herbicide antidotes.

BACKGROUND OF THE INVENTION

An herbicide is a compound which controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: pre-plant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes an amount of an herbicide compound which controls or modifies plant growth. The actual amount used depends upon several considerations, including particular weed susceptibility and overall cost limitations.

The most important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

To preserve the beneficial aspects of herbicide use and to minimize crop damage, many herbicide antidotes have been prepared. These antidotes reduce or eliminate damage to the crop without substantially impairing the damaging effect of the herbicide on weed species. See U.S. Pat. Nos. 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes an amount of an antidote compound which counteracts a phytotoxic response of a beneficial crop to an herbicide.

Thiocarbamate and acetanilide herbicides are particularly effective in the control of grassy type weeds which interfere with the cultivation of a wide variety of crops, e.g., barley, corn, cotton lentils, peanuts, peas, potatoes, soybeans, spinach, tobacco and tomatoes. Frequently the effective use of these herbicides requires the addition of an antidote compound.

DESCRIPTION OF THE INVENTION

It has now been discovered that certain haloalkylcarbonylamino-1,3dioxane compounds are effective antidotes for the protection of a variety of crops from thiocarbamate and acetanilide herbicide injuries. Such compounds have the following formula:

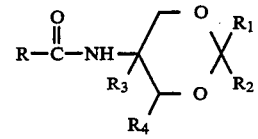

in which

R is haloalkyl wherein halo is chlorine, bromine or iodine and the alkyl group has 1–4 carbon atoms, inclusive;

$R_1$ is selected from the group consisting of hydrogen; lower alkyl having 1–4 carbon atoms, inclusive; alkenyl having 2–4 carbon atoms, inclusive, and phenyl;

$R_2$ is selected from the group consisting of hydrogen and lower alkyl having 1–4 carbon atoms, inclusive;

$R_3$ is selected from the group consisting of hydrogen and lower alkyl having 1–4 carbon atoms, inclusive;

$R_4$ is selected from the group consisting of hydrogen and a nitro group; and either $R_3$ is hydrogen or $R_4$ is hydrogen.

This invention also embodies a two-part herbicidal system comprised of (a) an herbicidally effective amount of a thiocarbamate compound of the formula

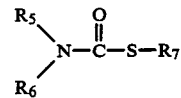

in which $R_5$ is alkyl having 1–6 carbon atoms, inclusive;

$R_6$ is selected from the group consisting of alkyl having 1–6 carbon atoms, inclusive; and cyclohexyl; or $R_5$ and $R_6$ form indistinguishable parts of a single alkylene ring having 4–10 carbon atoms, inclusive; and $R_7$ is selected from the group consisting of alkyl having 1–6 carbon atoms, inclusive; haloalkyl wherein halo is selected from the group consisting of chlorine, bromine and iodine and alkyl has 1–6 carbon atoms, inclusive; alkenyl having 2–6 carbon atoms, inclusive; halo alkenyl wherein halo is selected from the group consisting of chlorine, bromine and iodine and alkenyl has 2–6 carbon atoms, inclusive; benzyl; and halo-substituted benzyl, wherein halo is selected from the group consisting of chlorine, bromine and iodine; and (b) a non-phytotoxic antidotally effective amount of a compound of the formula

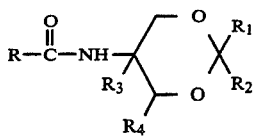

in which

R is selected from the group consisting of haloalkyl wherein halo is chlorine, bromine or iodine and the alkyl group has 1–4 carbon atoms, inclusive;

$R_1$ is selected from the group consisting of hydrogen; lower alkyl having 1–4 carbon atoms, inclusive; alkenyl having 2–4 carbon atoms, inclusive; and phenyl;

$R_2$ is selected from the group consisting of hydrogen and lower alkyl having 1–4 carbon atoms, inclusive;

$R_3$ is selected from the group consisting hydrogen and lower alkyl having 1–4 carbon atoms, inclusive;

$R_4$ is selected from the group consisting of hydrogen and a nitro group; and either $R_3$ is hydrogen or $R_4$ is hydrogen.

By way of exemplification, the active thiocarbamate herbicides employed in the invention may include the following: S-ethyl dipropyl thiocarbamate, S-ethyl diisobutyl thiocarbamate, S-propyl dipropyl thiocarbamate, S-propyl butylethylthiocarbamate, S-(2,3,3-trichloroallyl)diisopropyl thiocarbamate, S-ethyl N-ethyl N-cyclohexyl thiocarbamate, S-ethyl hexahydro-1H-azepine-1-carbothioate, isopropyl-1-hexahydro-1,4-azepine-1-carbothioate, S-benzyl N,N-disec-butylthiolcarbamate, S-(4-chlorobenzyl) N,N-diethyl thiolcarbamate and combinations thereof.

This invention also embodies a two-part herbicidal system comprised of (a) an herbicidally effective amount of an acetanilide compound of the formula

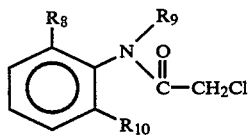

in which $R_8$ and $R_{10}$ are independently selected from the group consisting of hydrogen; and alkyl having 1–6 carbon atoms, inclusive; and $R_9$ is selected from the group consisting of alkyl having 1–6 carbon atoms, inclusive; alkoxy having 1–8 carbon atoms, inclusive; and carbethoxyalkyl wherein the alkyl group has 1–4 carbon atoms, inclusive; and (b) a non-phytotoxic antidotally effective amount of a compound of the formula

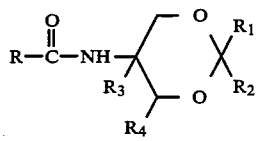

in which

R is haloalkyl wherein halo is chlorine, bromine or iodine and the alkyl group has 1–4 carbon atoms, inclusive;

$R_1$ is selected from the group consisting of hydrogen; lower alkyl having 1–4 carbon atoms, inclusive; alkenyl having 2–4 carbon atoms, inclusive; and phenyl;

$R_2$ is selected from the group consisting of hydrogen and lower alkyl having 1–4 carbon atoms, inclusive;

$R_3$ is selected from the group consisting of hydrogen and lower alkyl having 1–4 carbon atoms, inclusive;

$R_4$ is selected from the group consisting of hydrogen and a nitro group; and either $R_3$ is hydrogen or $R_4$ is hydrogen.

By way of exemplification, the active acetanilide compounds employed in the invention may include: 2-chloro-2',6'-diethyl-N(methoxymethyl) acetanilide; 2-chloro-2'-methyl-6'-ethyl-N(methoxypropyl-(2))-acetanilide; 2-chloro-2',6'-dimethyl-N-(methoxyethyl)acetanilide; 2-chloro-2'-methyl-6'-ethyl-N-(ethoxymethyl)acetanilide; 2-chloro-N-isopropyl acetanilide; 2-chloro-2',6'-diethyl-N-(n-butoxymethyl) acetanilide; and 2-chloro-N-carbethoxymethyl-2',6'diethyl acetanilide.

This invention also includes the method of establishing herbicidal selectivity which comprises applying to the locus where protection is desired an antidotally effective amount of a compound of the formula

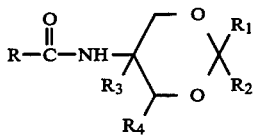

in which

R is haloalkyl wherein halo is chlorine, bromine or iodine and the alkyl group has 1–4 carbon atoms, inclusive;

$R_1$ is selected from the group consisting of hydrogen; lower alkyl having 1–4 carbon atoms, inclusive; alkenyl having 2–4 carbon atoms, inclusive; and phenyl;

$R_2$ is selected from the group consisting of hydrogen and lower alkyl having 1–4 carbon atoms, inclusive;

$R_3$ is selected from the group consisting of hydrogen and lower alkyl having 1–4 carbon atoms, inclusive;

$R_4$ is selected from the group consisting of hydrogen and a nitro group; and either $R_3$ is hydrogen or $R_4$ is hydrogen.

The locus where selectivity is desired may include soil, seeds, seedlings and vegetation.

Preparation

The thiocarbamates of the present composition are either commercially available or can be prepared by the procedures described in U.S. Pat. Nos. 2,913,327, 2,983,747, 3,133,947, 3,185,720 and 3,198,786.

The acetanilides of the present composition are either commercially available or can be prepared by the procedures described in U.S. Pat. Nos. 2,863,752; 3,442,945; 3,780,090; 3,937,730; 3,952,056; and 4,070,179.

The haloalkylcarbonylamino-1,3-dioxanes of this invention can be prepared according to the following general procedures, depending upon the starting materials.

In a first procedure, an appropriate haloalkylcarbonyl chloride is reacted with 5-methyl-5-amino-1,3-dioxane in a basic solution. The reaction is carried out at temperatures below 35° C. The reaction mixture may be stripped and the product recrystallized in ethanol/water. Structure may be confirmed by nuclear magnetic resonance (NMR) spectroscopy.

In an alternate procedure, an appropriate dialkoxy compound is reacted with an appropriate dihydroxyalkyl haloacetamide in an acidic solution. The reaction is carried out at elevated temperatures. Distillate is collected at 80° C. The distillate may be cooled and washed with sodium carbonate and water. The product may be obtained by removing the solvent in vacuum. Structure may be confirmed by NMR spectroscopy.

The following examples illustrate the preparation of specific compounds according to these general methods. (Compound numbers correspond to those in Tables I, IV and V).

EXAMPLE I (Compound No. 1)

Preparation of 5-methyl-5-(2′,3′-dibromopropionyl)amino-1,3-dioxane

Five and nine-tenths grams (g) (0.05 mole) of 5-methyl-5-amino-1,3-dioxane, 3.2 g (0.04 mole) of 50% sodium hydroxide, 8 milliliters (ml) of water and 55 ml of methylene chloride were combined in a reaction flask. The mixture was cooled to −10° C. Ten g (0.04 mole) of 2,3-dibromopropionyl chloride were added dropwise. The reaction mixture was stirred for 2 hours and then vacuum stripped. The product was recrystallized in ethanol/water. Yield was 8.7 g of 5-methyl-5-(2′,3′-dibromopropionyl)amino-1,3-dioxane. m.p.=115°–119° C. Structure was confirmed by NMR spectroscopy.

EXAMPLE II (Compound No. 4)

Preparation of 5-(2′-bromo-3′-chloropropionyl)amino-5-ethyl-1,3-dioxane

Five and two-tenths g (0.04 mole) of 5-ethyl-5-amino-1,3-dioxane, 3.2 g (0.04 mole) of 50% sodium hydroxide, 10 ml of water, and 90 ml of methylene chloride were combined in a reaction flask. The mixture was cooled to below 35° C. Eight and two-tenths g (0.04 mole) of 2-bromo-3chloropropionyl chloride were added dropwise. The mixture was stirred for ½ hour, filtered, dried over magnesium sulfate, and vacuum stripped. Yield was 10.8 g of 5-(2′-bromo-3′-chloropropionyl) amino-5-ethyl-1,3-dioxane. m.p.=95°–109° C. Structure was confirmed by NMR.

EXAMPLE III (Compound No. 10)

Preparation of 5-chloroacetylamino-5-ethyl-1,3-dioxane

Five and two-tenths g (0.04 mole) of 5-ethyl-5-amino-1,3-dioxane, 3.2 g (0.04 mole) of 50% sodium hydroxide, 10 ml of water, and 90 ml of methylene chloride were combined in a reaction flask. The mixture was cooled to below 35° C. Four and one-half g of chloroacetylchloride were added dropwise. The reaction mixture was stirred for one-half hour, washed with water and dried over magnesium sulfate. The solvent was vacuum stripped. Yield was 5.8 g of 5-chloroacetylamino-5-ethyl-1,3-dioxane. m.p.=89°–95° C. Structure was confirmed by NMR.

EXAMPLE IV (Compound No. 18)

Preparation of 2-vinyl-5-methyl-5-dichloroacetylamino-1,3-dioxane

This example illustrates use of the alternate general procedure.

Six and one-half grams (0.03 mole) of 2,2-(dimethoxyethyl) dichloroacetamide, 3.9 g (0.03 mole) of acrolein diethylacetal, 50 ml of acetonitrile and 0.2 g of ammonium chloride were combined in a reaction flask. The reaction mixture was stirred and refluxed through an attached packed column and variable take-off condenser. Distillate was removed to a head temperature of 78° C.

The reaction mixture was cooled to 40° C. and 0.1 g of crushed ammonium chloride was added. The mixture was heated to reflux and distillate was collected between 73° and 81° C. An additional 0.1 g of ammonium chloride was added and the temperature rose to 83° C. Heating was stopped and the hot reaction mixture was poured over ice and extracted twice with 75 ml of dichloromethane. The extracts were combined and washed with 100 ml of water. After drying, the solvent was removed in vacuo to yield 5.0 g of 2-vinyl-5-methyl-5-dichloroacetalamino-1,3-dioxane, an oil. $n_D^{30}=1.4980$. Structure was confirmed by NMR spectroscopy and gas chromatography.

EXAMPLE V (Compound No. 21)

Preparation of 2,2-dimethyl-4-(p-nitrophenyl)-5-dichloro-1,3-dioxane

This example demonstrates use of the alternate general procedure.

Six grams (0.019 mole) of chloroamphenicol, 2.3 g (0.022 mole) of acetone dimethylacetal, 0.2 g of -napthalene sulfonic acid and 60 ml of ethylene dichloride were combined in a reaction flask. The reaction mixture was stirred and refluxed through an attached packed column and variable take-off condenser. Distillate was removed to a head temperature of 80° C.

The distillate was cooled and washed with water, twice with sodium carbonate and a second time with water. The mixture was dried and stripped. Yield was 6.0 g of 2,2-dimethyl-4-(p-nitrophenyl)-5-dichloro-1,3-dioxane. m.p.=140°–143° C. Structure was confirmed by NMR.

TABLE I
HALOALKYLAMINO-1,3-DIOXANES

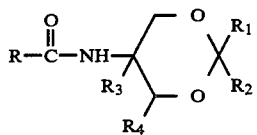

| Cmpd. No. | R | $R_1$ | $R_2$ | $R_3$ | $R_4$ | Chemical Name | Physical Constant |
|---|---|---|---|---|---|---|---|
| 1 | CH₂—CH (Br, Br) | H | H | CH₃ | H | 5-methyl-5-(2′,3′-dibromopropionyl)amino-1,3-dioxane | m.p. = 115–119° C. |
| 2 | CH₂—CH (Br, Br) | CH₃ | H | CH₃ | H | 5-(2,3-dibromopropionyl)amino-2,5-dimethyl-1,3-dioxane | m.p. = 124–128° C. |
| 3 | CH₂—CH (Br, Br) | H | H | C₂H₅ | H | 5-(2,3-dibromopropionyl)amino-5-ethyl-1,3-dioxane | m.p. = 100–107° C. |
| 4 | CH₂=CH | H | H | C₂H₅ | H | 5-(2′-bromo-3′-chloropropionyl)amino-5-ethyl-1,3-dioxane | m.p. = 95–109° C. |
| 5 | Cl₂CH | CH₃ | C₂H₅ | CH₃ | H | 2-ethyl-2,5-dimethyl-5-dichloroacetylamino-1,3-dioxane | m.p. = 84–87° C. |
| 6 | ClCH₂ | H | H | CH₃ | H | 5-chloroacetylamino-5-methyl-1,3-dioxane | m.p. = 116–120° C. |
| 7 | Cl₂CH | H | H | CH₃ | H | 5-dichloroacetylamino-5-methyl-1,3-dioxane | m.p. = 127° C. |
| 8 | ClCH₂ | CH₃ | H | CH₃ | H | 5-chloroacetylamino-2,5-dimethyl-1,3-dioxane | m.p. = 94–97° C. |
| 9 | Cl₂CH | CH₃ | H | CH₃ | H | 5-dichloroacetylamino-2,5-dimethyl-1,3-dioxane | m.p. = 104–106° C. |
| 10 | ClCH₂ | H | H | C₂H₅ | H | 5-chloroacetylamino-5-ethyl-1,3-dioxane | m.p. = 89–94° C. |
| 11 | Cl₂CH | H | H | C₂H₅ | H | 5-(dichloroacetylamino)-5-ethyl-1,3-dioxane | m.p. = 94–96.5° C. |
| 12 | ClCH₂ | CH₃ | CH₃ | CH₃ | H | 5-methyl-5-chloroacetylamino-2,2-dimethyl-1,3-dioxane | $n_D^{30}$ = 1.4785 |
| 13 | Cl₂CH | CH₃ | CH₃ | CH₃ | H | 2,2,5-trimethyl-5-dichloroacetylamino-1,3-dioxane | m.p. = 101–104° C. |
| 14 | ClCH₂ | CH₃ | CH₃ | C₂H₅ | H | 2,2-dimethyl-5-ethyl-5-chloroacetylamino-1,3-dioxane | m.p. = 67–70° C. |
| 15 | Cl₂CH | CH₃ | CH₃ | C₂H₅ | H | 2,2-dimethyl-5-ethyl-5-dichloroacetylamino-1,3-dioxane | m.p. = 90–93° C. |
| 16 | ClCH₂ | C₂H₅ | CH₃ | CH₃ | H | 2,5-dimethyl-2-ethyl-5-chloroacetylamino-1,3-dioxane | m.p. = 62–69° C. |
| 17 | ClCH₂ | CH=CH₂ | H | CH₃ | H | 2-allyl-5-methyl-chloroacetylamino-1,3-dioxane | m.p. = 78–83° C. |
| 18 | Cl₂CH | CH=CH₂ | H | CH₃ | H | 2-allyl-5-methyl-5-dichloroacetylamino-1,3-dioxane | $n_D^{30}$ = 1.4980 |
| 19 | ClCH₂ | C₆H₅ | H | CH₃ | H | 2-phenyl-5-methyl-5-chloroacetylamino-1,3-dioxane | softened above 95° C. |
| 20 | Cl₂CH | C₆H₅ | H | CH₃ | H | 2-phneyl-5-methyl-5-dichloroacetylamino-1,3-dioxane | m.p. = 145–148° C. |
| 21 | Cl₂CH | CH₃ | CH₃ | H | p-NO₂-C₆H₄ | 2,2-dimethyl-4-(p-nitrophenyl)-5-dichloroacetylamino-1,3-dioxane | m.p. = 140–143° C. |
| 22 | Cl₂CH | CH₃ | H | H | p-NO₂-C₆H₄ | 2-methyl-4-(p-nitrophenyl)-5-dichloroacetylamino-1,3-dioxane | glass |

Testing

Stock solutions of the herbicides were prepared by diluting the requisite amount of each herbicide in water. Examples of solution compositions and application rates are summarized in Table II.

TABLE II

| | Herbicide Stock Solutions | | | |
|---|---|---|---|---|
| | Composition | | Application | |
| Herbicide Name | Herbicide (mg)* | Water (ml) | ml/flat** | lb/acre |
| VERNAM ® 6E S—propyl N,N—dipropyl thiocarbamate | 533 | 400 | 5 | 1.25 |
| | 3000 | 500 | 5 | 6.00 |
| EPTAM ® 6E S—ethyl N,N—dipropyl thiocarbamate | 2225 | 350 | 5 | 6.00 |

*The weight is measured in terms of mg of formulated herbicide. The formulations used contain about 72% active herbicide compound.
**The flats measure 5.95 inches by 9.5 inches. Approximately four (4) mg/flat is equal to one (1) lb/acre.

The herbicide was either incorporated into the soil prior to planting or applied to the soil after planting and prior to emergence of the plants. In some cases of pre-plant incorporation, the herbicide was incorporated into the soil alone in preparation for in-furrow application of the antidote; in others the herbicide solution was tank-mixed with the antidote solution prior to incorporation.

Stock solutions of each antidote compound were prepared at the desired concentrations by diluting the requisite amount of each antidote in acetone. Examples of solution compositions, rates and application methods are summarized in Table III.

TABLE III

| Antidote Stock Solutions | | | | |
|---|---|---|---|---|
| Antidote: Haloalkylamino-1,3-dioxanes | | | | |
| Composition | | Application | | |
| Antidote (mg) | Acetone (ml) | ml/flat | lb/acre | Method |
| 95 | 15 | 1.50 | 5.00 | IF* |
| 60 | 15 | 5.00 | 5.00 | PPI** |

*IF = In-furrow surface application of antidote.
**PPI = Pre-plant incorporation of tank-mixed solution of herbicide and antidote The antidote solutions were applied to the soil either by in-furrow surface application or by pre-plant incorporation. In all cases of pre-plant incorporation, the antidote was tank-mixed with the herbicide prior to incorporation into the soil.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only. All flats were placed on greenhouse benches where temperature was maintanined between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thio]-4-cyclohexene-1,2-dicarboximide, and 18-18-18 fertilizer, which contains 18% by weight equivalent each of nitrogen, phosphorus pentoxide, and potassium oxide.

Injury ratings were taken four weeks after application of the antidote. The effectiveness of the antidote was determined by visual comparison of crop injury in the test flats to that in the control flats.

The treated crops initially screened for diminution of herbicidal injury were milo, wheat, rice, barley, corn and soybeans. Compounds which showed substantial activity were tested further. The herbicides and the most active antidote compositions were then screened on weed species. The weed species tested included watergrass (*Echinochloa crusgalli*), foxtail (*Setaria viridis*), wild oat (*Avena fatua*), shattercane (*Sorghum bicolor*), johnsongrass (*Sorghum halepense*) and mustard (*Brassiica juncea*).

KEY TO TABLES IV AND V

Compound numbers in these tables correspond to the numbers and their chemical description in Table I. Compounds omitted in Table V were not tested on weed species.

Herbicides

VERNAM ®—S-propyl N,N-dipropyl thiocarbamate
EPTAM ®—S-ethyl N,N-dipropyl thiocarbamate
RONEET ®—S-ethyl N-ethyl-N-cyclohexyl thiocarbamate
SUTAN ®—S-ethyl N,N-diisobutyl thiocarbamate
LASSO ®—2-chloro-2',6'-diethyl-N-(methoxymethyl)acetanilide
TERIDOX ®—2-chloro-2',6'-dimethyl-N-(methoxyethyl)acetanilide
TREFLAN ®—α,α,α-trifluoro-2,6-dinitro-N,N-dipropyl-p-toluidine
ATRAZINE ®—2-chloro-4-ethylamino-6-isopropylamino-S-triazine

Application Methods

PES = Surface application of herbicide to soil after planting of seeds and prior to emergence of plants.
IF = In-furrow surface application of antidote (soil previously treated with herbicide only).
PPI = Pre-plant incorporation of herbicide or antidote. If both herbicide and antidote were preplant incorporated, a tank-mixed solution was used.
TM = Tank-mixed solution of herbicide and antidote.

If no antidote was applied, the word "none" appears in the Antidote Rate column. The results shown on this line are the percent injuries sustained by each of the crops when treated with the herbicide only at the rate specified.

All rates shown, for both herbicide and antidote, are in pounds per acre.

Injury Ratings

The injury to the crop (Table IV) or weeds (Table V) is shown as a percentage of damage done to the plants as compared to an evaluation of the undamaged state of the plants. The damage done to the plants is a function of the number of plants injured and the extent of injury to each plant. This rating is made four (4) weeks after application of the herbicide alone or of the herbicide in combination with the antidote.

An asterisk (*) in Table IV indicates that the antidote compound is active in reducing herbicidal injury to the crop. Parentheses around a number indicate that the test has been run more than once and the results are inconclusive.

Table V shows that the antidote compounds tested have no effect on weeds, i.e., herbicidal injury to the weeds is sustained even in the presence of an antidote compound.

TABLE IV

Antidotal Effectiveness

| Cmpd. No. | Herbicide | Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
| 1 | VERNAM | 1.0 | PPI | none | — | 100 | 77 | 50 | 87 | 83 | | |
|   | VERNAM | 1.0 | PPI | 5.0 | IF | 100 | *60 | 50 | 87 | *20 | | |
|   | VERNAM | 6.0 | PPI | none | — | | | | | | 90 | 100 |
|   | VERNAM | 6.0 | PPI | 5.0 | IF | | | | | | *20 | *80 |
|   | VERNAM | 1.0 | PPI | none | — | | | | | 60 | | |
|   | VERNAM | 1.0 | PPI | 1.0 | IF | | | | | *30 | | |
|   | VERNAM | 1.0 | PPI | 5.0 | IF | | | | | *10 | | |
|   | VERNAM | 1.0 | PPI | none | — | | 100 | | | | | |
|   | VERNAM | 1.0 | PPI | 1.0 | IF | | *70 | | | | | |
|   | VERNAM | 1.0 | PPI | 5.0 | IF | | *60 | | | | | |
|   | VERNAM | 6.0 | PPI | none | — | | | | | | | 60 |
|   | VERNAM | 6.0 | PPI/TM | 1.0 | PPI/TM | | | | | | | 60 |
|   | VERNAM | 6.0 | PPI/TM | 5.0 | PPI/TM | | | | | | | 60 |
|   | VERNAM | 6.0 | PPI | none | — | | | | | | | 60 |
|   | VERNAM | 6.0 | PPI/TM | 1.0 | PPI/TM | | | | | | | 60 |
|   | VERNAM | 6.0 | PPI/TM | 5.0 | PPI/TM | | | | | | | 60 |
|   | EPTAM | 6.0 | PPI | none | — | | | | | 80 | | |
|   | EPTAM | 6.0 | PPI | 0.5 | PPI | | | | | *70 | | |
|   | EPTAM | 6.0 | PPI | 5.0 | PPI | | | | | *50 | | |
|   | LASSO | 3.0 | PES | none | — | 98 | 70 | | 99 | | | |
|   | LASSO | 3.0 | PES | 5.0 | IF | 98 | 70 | | *95 | | | |
|   | LASSO | 3.0 | PES | none | — | 90 | 55 | | | | | |
|   | LASSO | 3.0 | PES/TM | 5.0 | PES/TM | 90 | *40 | | | | | |
|   | LASSO | 4.0 | PES | none | — | | | | 80 | | | |
|   | LASSO | 4.0 | PES/TM | 5.0 | PES/TM | | | | *20 | | | |
|   | TREFLAN | 1.0 | PPI | none | — | 100 | 98 | | 100 | 85 | | |
|   | TREFLAN | 1.0 | PPI | 5.0 | IF | 100 | 98 | | 100 | 85 | | |
| 2 | VERNAM | 1.0 | PPI | none | — | 100 | 75 | 70 | 95 | 70 | | |
|   | VERNAM | 1.0 | PPI | 5.0 | IF | *80 | *60 | 70 | 95 | *50 | | |
|   | VERNAM | 6.0 | PPI | none | — | | | | | | | 80 |
|   | VERNAM | 6.0 | PPI | 5.0 | IF | | | | | | | 80 |
|   | VERNAM | 6.0 | PPI | none | — | | | | | 90 | | |
|   | VERNAM | 6.0 | PPI | 5.0 | IF | | | | | *50 | | |
|   | VERNAM | 1.25 | PPI | none | — | | | | | 70 | | |
|   | VERNAM | 1.25 | PPI | 1.0 | IF | | | | | *40 | | |
|   | VERNAM | 1.25 | PPI | 5.0 | IF | | | | | *30 | | |
|   | VERNAM | 1.25 | PPI | none | — | | | | | 70 | | |
|   | VERNAM | 1.25 | PPI/TM | 1.0 | PPI/TM | | | | | *50 | | |
|   | VERNAM | 1.25 | PPI/TM | 5.0 | PPI/TM | | | | | *35 | | |
|   | LASSO | 3.5 | PES | none | — | 95 | 70 | | 100 | 70 | | |
|   | LASSO | 3.5 | PES | 5.0 | IF | *60 | 70 | | 100 | *50 | | |
|   | TERIDOX | 1.0 | PES | none | — | 100 | 70 | | | 80 | 100 | |
|   | TERIDOX | 1.0 | PES | 5.0 | IF | 100 | 70 | | | *55 | 100 | |
| 3 | VERNAM | 1.0 | PPI | none | — | 95 | 70 | 70 | 95 | 50 | | |
|   | VERNAM | 1.0 | PPI | 5.0 | IF | 95 | *30 | 80 | 95 | *0 | | |
|   | VERNAM | 6.0 | PPI | none | — | | | | | | 70 | 55 |
|   | VERNAM | 6.0 | PPI | 5.0 | IF | | | | | | *30 | *40 |
|   | VERNAM | 1.25 | PPI | none | — | | 95 | | 95 | 80 | | |
|   | VERNAM | 1.25 | PPI | 1.0 | IF | | 95 | | 95 | *60 | | |
|   | VERNAM | 1.25 | PPI | 5.0 | IF | | *60 | | 95 | *40 | | |
|   | VERNAM | 5.0 | PPI | none | — | | | | | | | 40 |
|   | VERNAM | 5.0 | PPI | 1.0 | IF | | | | | | | 40 |
|   | VERNAM | 5.0 | PPI | 5.0 | IF | | | | | | | *30 |
|   | EPTAM | 6.0 | PPI | none | — | | | | | 80 | | |
|   | EPTAM | 6.0 | PPI | 0.5 | PPI | | | | | *10 | | |
|   | EPTAM | 6.0 | PPI | 5.0 | PPI | | | | | *30 | | |
|   | SUTAN | 5.0 | PPI | none | — | | | | 35 | | | |
|   | SUTAN | 5.0 | PPI/TM | 1.0 | PPI/TM | | | | 35 | | | |
|   | SUTAN | 5.0 | PPI/TM | 5.0 | PPI/TM | | | | *20 | | | |
|   | LASSO | 3.0 | PES | none | — | 90 | 55 | | | | | |
|   | LASSO | 3.0 | PES/TM | 5.0 | PES/TM | *80 | *35 | | | | | |
|   | LASSO | 4.0 | PES | none | — | | | | 80 | | | |
|   | LASSO | 4.0 | PES/TM | 5.0 | PES/TM | | | | *20 | | | |
| 4 | VERNAM | 1.25 | PPI | none | — | 100 | 95 | 60 | 95 | 95 | | |
|   | VERNAM | 1.25 | PPI | 5.0 | IF | *40 | *60 | 60 | 95 | *20 | | |
|   | VERNAM | 6.0 | PPI | none | — | | | | | | 85 | 60 |
|   | VERNAM | 6.0 | PPI | 5.0 | IF | | | | | | *0 | 60 |
|   | VERNAM | 1.25 | PPI | none | — | | | | | 95 | | |
|   | VERNAM | 1.25 | PPI | 1.0 | IF | | | | | *40 | | |
|   | VERNAM | 1.25 | PPI | 5.0 | IF | | | | | *20 | | |
|   | VERNAM | 1.25 | PPI | none | — | | | | | 90 | | |

TABLE IV-continued

Antidotal Effectiveness

| Cmpd. No. | Herbicide | Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
|   | VERNAM | 1.25 | PPI/TM | 0.25 | PPI/TM |   |   |   |   | 90 |   |   |
|   | VERNAM | 1.25 | PPI/TM | 0.5 | PPI/TM |   |   |   |   | 90 |   |   |
|   | VERNAM | 1.25 | PPI/TM | 1.0 | PPI/TM |   |   |   |   | *70 |   |   |
|   | EPTAM | 6.0 | PPI | none | — |   |   |   |   |   | 80 |   |
|   | EPTAM | 6.0 | PPI | 0.5 | PPI |   |   |   |   |   | *0 |   |
|   | EPTAM | 6.0 | PPI | 5.0 | PPI |   |   |   |   |   | *0 |   |
|   | RONEET | 3.0 | PPI | none | — | 90 |   |   |   |   |   |   |
|   | RONEET | 3.0 | PPI | 1.0 | IF | *60 |   |   |   |   |   |   |
|   | RONEET | 3.0 | PPI | 5.0 | IF | 90 |   |   |   |   |   |   |
|   | LASSO | 3.0 | PES | none | — | 98 | 70 |   | 99 |   |   |   |
|   | LASSO | 3.0 | PES | 5.0 | IF | *85 | *55 |   | 99 |   |   |   |
|   | LASSO | 3.5 | PES | none | — | 95 | 70 |   | 100 | 70 |   |   |
|   | LASSO | 3.5 | PES | 5.0 | IF | *10 | *20 |   | 100 | *15 |   |   |
|   | TERIDOX | 1.0 | PES | none | — | 100 | 70 |   | 80 | 100 |   |   |
|   | TERIDOX | 1.0 | PES | 5.0 | IF | *90 | *35 |   | *35 | *0 |   |   |
|   | ATRAZINE | 1.0 | PES | none | — |   | 100 | 70 | 100 |   |   |   |
|   | ATRAZINE | 1.0 | PES | 5.0 | IF |   | 100 | 70 | 100 |   |   |   |
|   | ATRAZINE | 0.25 | PES | none | — |   |   |   |   |   |   | 100 |
|   | ATRAZINE | 0.25 | PES | 5.0 | IF |   |   |   |   |   |   | 100 |
|   | TREFLAN | 1.0 | PPI | none | — | 100 | 98 |   | 100 | 85 |   |   |
|   | TREFLAN | 1.0 | PPI | 5.0 | IF | 100 | *90 |   | 100 | 85 |   |   |
| 5 | VERNAM | 1.25 | PPI | none | — | 100 | 100 | 60 | 100 | 90 |   |   |
|   | VERNAM | 1.25 | PPI | 5.0 | IF | *75 | *90 | *50 | *90 | *70 |   |   |
|   | VERNAM | 6.0 | PPI | none | — |   |   |   |   |   | 95 | 60 |
|   | VERNAM | 6.0 | PPI | 5.0 | IF |   |   |   |   |   | *70 | 60 |
| 6 | VERNAM | 1.0 | PPI | none | — | 100 | 77 | 50 | 87 | 83 |   |   |
|   | VERNAM | 1.0 | PPI | 5.0 | IF | *60 | *60 | 50 | 87 | *60 |   |   |
|   | VERNAM | 6.0 | PPI | none | — |   |   |   |   |   | 90 | 60 |
|   | VERNAM | 6.0 | PPI | 5.0 | IF |   |   |   |   |   | *0 | 90 |
|   | VERNAM | 1.0 | PPI | none | — |   | 100 |   |   |   |   |   |
|   | VERNAM | 1.0 | PPI | 1.0 | IF |   | 100 |   |   |   |   |   |
|   | VERNAM | 1.0 | PPI | 5.0 | IF |   | 100 |   |   |   |   |   |
|   | VERNAM | 6.0 | PPI | none | — |   |   |   |   |   |   | 60 |
|   | VERNAM | 6.0 | PPI/TM | 1.0 | PPI/TM |   |   |   |   |   |   | *(45) |
|   | VERNAM | 6.0 | PPI/TM | 2.0 | PPI/TM |   |   |   |   |   |   | *50 |
|   | VERNAM | 6.0 | PPI/TM | 5.0 | PPI/TM |   |   |   |   |   |   | 60 |
|   | VERNAM | 6.0 | PPI | none | — |   |   |   |   |   |   | 60 |
|   | VERNAM | 6.0 | PPI/TM | 1.0 | PPI/TM |   |   |   |   |   |   | (60) |
|   | VERNAM | 6.0 | PPI/TM | 5.0 | PPI/TM |   |   |   |   |   |   | 60 |
|   | VERNAM | 6.0 | PPI | none | — |   |   |   |   |   |   | 60 |
|   | VERNAM | 6.0 | PPI/TM | 1.0 | PPI/TM |   |   |   |   |   |   | *(0) |
|   | VERNAM | 6.0 | PPI/TM | 5.0 | PPI/TM |   |   |   |   |   |   | 60 |
|   | EPTAM | 6.0 | PPI | none | — |   |   |   |   |   | 80 |   |
|   | EPTAM | 6.0 | PPI | 0.5 | PPI |   |   |   |   |   | *30 |   |
|   | EPTAM | 6.0 | PPI | 5.0 | PPI |   |   |   |   |   | *0 |   |
|   | LASSO | 3.0 | PES | none | — | 98 | 70 |   | 99 |   |   |   |
|   | LASSO | 3.0 | PES | 5.0 | IF | 98 | 70 |   | 99 |   |   |   |
|   | ATRAZINE | 0.25 | PES | none | — |   |   |   |   |   |   | 100 |
|   | ATRAZINE | 0.25 | PES | 5.0 | IF |   |   |   |   |   |   | 100 |
|   | ATRAZINE | 1.0 | PES | none | — |   | 100 | 70 | 100 |   |   |   |
|   | ATRAZINE | 1.0 | PES | 5.0 | IF |   | 100 | 70 | 100 |   |   |   |
|   | TREFLAN | 1.0 | PPI | none | — | 100 | 98 |   | 100 | 85 |   |   |
|   | TREFLAN | 1.0 | PPI | 5.0 | IF | 100 | *95 |   | 100 | *80 |   |   |
| 7 | VERNAM | 1.0 | PPI | none | — | 100 | 77 | 50 | 87 | 83 |   |   |
|   | VERNAM | 1.0 | PPI | 5.0 | IF | 100 | 77 | *40 | 87 | 83 |   |   |
|   | VERNAM | 6.0 | PPI | none | — |   |   |   |   |   | 90 | 60 |
|   | VERNAM | 6.0 | PPI | 5.0 | IF |   |   |   |   |   | *40 | 90 |
|   | VERNAM | 6.0 | PPI | none | — |   |   |   |   |   |   | 60 |
|   | VERNAM | 6.0 | PPI/TM | 1.0 | PPI/TM |   |   |   |   |   |   | 60 |
|   | VERNAM | 6.0 | PPI/TM | 5.0 | PPI/TM |   |   |   |   |   |   | 75 |
| 8 | VERNAM | 1.0 | PPI | none | — | 100 | 75 | 70 | 95 | 70 |   |   |
|   | VERNAM | 1.0 | PPI | 5.0 | IF | *30 | 75 | 70 | 95 | *20 |   |   |
|   | VERNAM | 6.0 | PPI | none | — |   |   |   |   |   |   | 80 |
|   | VERNAM | 6.0 | PPI | 5.0 | IF |   |   |   |   |   |   | 100 |
|   | VERNAM | 6.0 | PPI | none | — |   |   |   |   |   | 90 |   |
|   | VERNAM | 6.0 | PPI | 5.0 | IF |   |   |   |   |   | *0 |   |
|   | VERNAM | 1.25 | PPI | none | — |   |   |   |   | 70 |   |   |
|   | VERNAM | 1.25 | PPI | 1.0 | IF |   |   |   |   | 70 |   |   |
|   | VERNAM | 1.25 | PPI | 5.0 | IF |   |   |   |   | 70 |   |   |
|   | VERNAM | 6.0 | PPI | none | — |   |   |   |   |   |   | 60 |
|   | VERNAM | 6.0 | PPI/TM | 1.0 | PPI/TM |   |   |   |   |   |   | 60 |
|   | VERNAM | 6.0 | PPI/TM | 5.0 | PPI/TM |   |   |   |   |   |   | 60 |
|   | EPTAM | 6.0 | PPI | none | — |   |   |   |   |   | 80 |   |
|   | EPTAM | 6.0 | PPI | 0.5 | PPI |   |   |   |   |   | *30 |   |
|   | EPTAM | 6.0 | PPI | 5.0 | PPI |   |   |   |   |   | *0 |   |
|   | RONEET | 4.0 | PPI | none | — | 60 |   |   |   |   |   |   |
|   | RONEET | 4.0 | PPI | 1.0 | IF | 60 |   |   |   |   |   |   |
|   | RONEET | 4.0 | PPI | 5.0 | IF | *20 |   |   |   |   |   |   |
|   | LASSO | 3.0 | PES | none | — | 98 | 70 |   | 99 |   |   |   |

TABLE IV-continued

| Cmpd. No. | Herbicide | Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
| | LASSO | 3.0 | PES | 5.0 | IF | 98 | 70 | | 99 | | | |
| | LASSO | 3.5 | PES | none | — | 95 | 70 | | 100 | 70 | | |
| | LASSO | 3.5 | PES | 5.0 | IF | 95 | *60 | | 100 | 70 | | |
| | TERIDOX | 1.0 | PES | none | — | 100 | 70 | | | 80 | 100 | |
| | TERIDOX | 1.0 | PES | 5.0 | IF | 100 | 70 | | | 80 | 100 | |
| | ATRAZINE | 0.25 | PES | none | — | | | | | | | 100 |
| | ATRAZINE | 0.25 | PES | 5.0 | IF | | | | | | | 100 |
| | ATRAZINE | 1.0 | PES | none | — | | | 100 | 70 | 100 | | |
| | ATRAZINE | 1.0 | PES | 5.0 | IF | | | 100 | 70 | 100 | | |
| | TREFLAN | 1.0 | PPI | none | — | 100 | 98 | | 100 | 98 | | |
| | TREFLAN | 1.0 | PPI | 5.0 | IF | 100 | 98 | | 100 | 98 | | |
| 9 | VERNAM | 1.0 | PPI | none | — | 100 | 75 | 70 | 95 | 70 | | |
| | VERNAM | 1.0 | PPI | 5.0 | IF | *90 | 75 | 70 | *50 | *60 | | |
| | VERNAM | 6.0 | PPI | none | — | | | | | | | 80 |
| | VERNAM | 6.0 | PPI | 5.0 | IF | | | | | | | 95 |
| | VERNAM | 6.0 | PPI | none | — | | | | | | 90 | |
| | VERNAM | 6.0 | PPI | 5.0 | IF | | | | | | *0 | |
| | VERNAM | 6.0 | PPI | none | — | | | | | | | 60 |
| | VERNAM | 6.0 | PPI/TM | 1.0 | PPI/TM | | | | | | | 60 |
| | VERNAM | 6.0 | PPI/TM | 5.0 | PPI/TM | | | | | | | 60 |
| | VERNAM | 6.0 | PPI | none | — | | | | | | | 60 |
| | VERNAM | 6.0 | PPI/TM | 5.0 | PPI/TM | | | | | | | 80 |
| | EPTAM | 6.0 | PPI | none | — | | | | | | 80 | |
| | EPTAM | 6.0 | PPI | 0.5 | PPI | | | | | | *70 | |
| | EPTAM | 6.0 | PPI | 5.0 | PPI | | | | | | *45 | |
| 10 | VERNAM | 1.25 | PPI | none | — | 80 | 80 | 70 | 95 | 70 | | |
| | VERNAM | 1.25 | PPI | 5.0 | IF | *30 | *60 | *50 | 95 | *50 | | |
| | VERNAM | 6.0 | PPI | none | — | | | | | | 90 | 50 |
| | VERNAM | 6.0 | PPI | 5.0 | IF | | | | | | *0 | *30 |
| | VERNAM | 5.0 | PPI | none | — | | | | | | | 65 |
| | VERNAM | 5.0 | PPI | 1.0 | IF | | | | | | | *50 |
| | VERNAM | 5.0 | PPI | 5.0 | IF | | | | | | | 80 |
| | EPTAM | 6.0 | PPI | none | — | | | | | | 90 | |
| | EPTAM | 6.0 | PPI/TM | 0.05 | PPI/TM | | | | | | 90 | |
| | EPTAM | 6.0 | PPI/TM | 0.5 | PPI/TM | | | | | | 90 | |
| | EPTAM | 6.0 | PPI/TM | 5.0 | PPI/TM | | | | | | *35 | |
| | EPTAM | 6.0 | PPI | none | — | | | | | | 90 | |
| | EPTAM | 6.0 | PPI/TM | 0.5 | PPI/TM | | | | | | *30 | |
| | EPTAM | 6.0 | PPI/TM | 5.0 | PPI/TM | | | | | | *20 | |
| | RONEET | 4.0 | PPI | none | — | 60 | | | | | | |
| | RONEET | 4.0 | PPI | 1.0 | IF | 60 | | | | | | |
| | RONEET | 4.0 | PPI | 5.0 | IF | 60 | | | | | | |
| 11 | VERNAM | 1.25 | PPI | none | — | 80 | 80 | 70 | 95 | 70 | | |
| | VERNAM | 1.25 | PPI | 5.0 | IF | *40 | *60 | 70 | 95 | *50 | | |
| | VERNAM | 6.0 | PPI | none | — | | | | | | 90 | 50 |
| | VERNAM | 6.0 | PPI | 5.0 | IF | | | | | | *0 | 70 |
| | EPTAM | 6.0 | PPI | none | — | | | | | | 90 | |
| | EPTAM | 6.0 | PPI/TM | 0.05 | PPI/TM | | | | | | 90 | |
| | EPTAM | 6.0 | PPI/TM | 0.5 | PPI/TM | | | | | | (90) | |
| | EPTAM | 6.0 | PPI/TM | 5.0 | PPI/TM | | | | | | *80 | |
| | EPTAM | 6.0 | PPI | none | — | | | | | | 90 | |
| | EPTAM | 6.0 | PPI/TM | 0.5 | PPI/TM | | | | | | *(55) | |
| | EPTAM | 6.0 | PPI/TM | 5.0 | PPI/TM | | | | | | *25 | |
| | RONEET | 4.0 | PPI | none | — | 60 | | | | | | |
| | RONEET | 4.0 | PPI | — | — | 60 | | | | | | |
| | RONEET | 4.0 | PPI | — | — | *40 | | | | | | |
| 12 | VERNAM | 1.25 | PPI | none | — | 100 | 95 | 60 | 100 | 90 | | |
| | VERNAM | 1.25 | PPI | 5.0 | IF | *60 | *60 | 60 | 100 | *60 | | |
| | VERNAM | 6.0 | PPI | none | — | | | | | | 85 | 70 |
| | VERNAM | 6.0 | PPI | 5.0 | IF | | | | | | *0 | 70 |
| | EPTAM | 6.0 | PPI | none | — | | | | | | 90 | |
| | EPTAM | 6.0 | PPI/TM | 0.05 | PPI/TM | | | | | | 90 | |
| | EPTAM | 6.0 | PPI/TM | 0.5 | PPI/TM | | | | | | *80 | |
| | EPTAM | 6.0 | PPI/TM | 5.0 | PPI/TM | | | | | | *0 | |
| | EPTAM | 6.0 | PPI | none | — | | | | | | 90 | |
| | EPTAM | 6.0 | PPI/TM | 0.5 | PPI/TM | | | | | | *40 | |
| | EPTAM | 6.0 | PPI/TM | 5.0 | PPI/TM | | | | | | *10 | |
| | EPTAM | 6.0 | PPI | none | — | | | | | | 70 | |
| | EPTAM | 6.0 | PPI | 0.5 | PPI | | | | | | *40 | |
| | EPTAM | 6.0 | PPI | 5.0 | PPI | | | | | | *0 | |
| 13 | VERNAM | 1.25 | PPI | none | — | 100 | 90 | 60 | 95 | 85 | | |
| | VERNAM | 1.25 | PPI | 5.0 | IF | 100 | 90 | 60 | 95 | 85 | | |
| | VERNAM | 6.0 | PPI | none | — | | | | | | 90 | 65 |
| | VERNAM | 6.0 | PPI | 5.0 | IF | | | | | | *65 | 70 |
| 14 | VERNAM | 1.25 | PPI | none | — | 100 | 95 | 70 | 100 | 95 | | |
| | VERNAM | 1.25 | PPI | 5.0 | IF | 100 | 95 | *55 | 100 | 95 | | |
| | VERNAM | 6.0 | PPI | none | — | | | | | | 90 | 65 |
| | VERNAM | 6.0 | PPI | 5.0 | IF | | | | | | *80 | *40 |
| 15 | VERNAM | 1.25 | PPI | none | — | 100 | 95 | 70 | 100 | 95 | | |

TABLE IV-continued

Antidotal Effectiveness

| Cmpd. No. | Herbicide | Rate | Herbicide Method | Antidote Rate | Antidote Method | Milo % Inj | Wheat % Inj | Cotton % Inj | Rice % Inj | Barley % Inj | Corn % Inj | Soybean % Inj |
|---|---|---|---|---|---|---|---|---|---|---|---|---|
|  | VERNAM | 1.25 | PPI | 5.0 | IF | 100 | 95 | *40 | 100 | *80 |  |  |
|  | VERNAM | 6.0 | PPI | none | — |  |  |  |  |  | 90 | 65 |
|  | VERNAM | 6.0 | PPI | 5.0 | IF |  |  |  |  |  | *80 | 65 |
|  | VERNAM | 1.25 | PPI | none | — |  |  |  | 50 |  |  |  |
|  | VERNAM | 1.25 | PPI | 1.0 | IF |  |  |  | 50 |  |  |  |
|  | VERNAM | 1.25 | PPI | 5.0 | IF |  |  |  | *20 |  |  |  |
| 16 | VERNAM | 1.25 | PPI | none | — | 100 | 95 | 70 | 100 | 95 |  |  |
|  | VERNAM | 1.25 | PPI | 5.0 | IF | 100 | 95 | 70 | 100 | 100 |  |  |
|  | VERNAM | 6.0 | PPI | none | — |  |  |  |  |  | 90 | 65 |
|  | VERNAM | 6.0 | PPI | 5.0 | IF |  |  |  |  |  | *30 | *50 |
|  | EPTAM | 5.0 | PPI | none | — |  |  |  |  |  | 85 |  |
|  | EPTAM | 5.0 | PPI/TM | 0.05 | PPI/TM |  |  |  |  |  | *60 |  |
|  | EPTAM | 5.0 | PPI/TM | 0.5 | PPI/TM |  |  |  |  |  | *0 |  |
|  | EPTAM | 5.0 | PPI/TM | 5.0 | PPI/TM |  |  |  |  |  | *0 |  |
| 17 | VERNAM | 1.25 | PPI | none | — | 100 | 100 | 60 | 100 | 90 |  |  |
|  | VERNAM | 1.25 | PPI | 5.0 | IF | *80 | *95 | 60 | 100 | *80 |  |  |
|  | VERNAM | 6.0 | PPI | none | — |  |  |  |  |  | 95 | 60 |
|  | VERNAM | 6.0 | PPI | 5.0 | IF |  |  |  |  |  | *85 | 60 |
| 18 | VERNAM | 1.25 | PPI | none | — | 90 | 75 | 55 | 90 | 60 |  |  |
|  | VERNAM | 1.25 | PPI | 5.0 | IF | *80 | *60 | 55 | *50 | *45 |  |  |
|  | VERNAM | 6.0 | PPI | none | — |  |  |  |  |  | 90 | 60 |
|  | VERNAM | 6.0 | PPI | 5.0 | IF |  |  |  |  |  | *30 | 60 |
|  | VERNAM | 1.0 | PPI | none | — |  |  |  | 98 |  |  |  |
|  | VERNAM | 1.0 | PPI | 1.0 | IF |  |  |  | *60 |  |  |  |
|  | VERNAM | 1.0 | PPI | 5.0 | IF |  |  |  | *20 |  |  |  |
|  | VERNAM | 1.25 | PPI | none | — |  |  |  |  | 85 |  |  |
|  | VERNAM | 1.25 | PPI | 1.0 | IF |  |  |  |  | 85 |  |  |
|  | VERNAM | 1.25 | PPI | 5.0 | IF |  |  |  |  | 85 |  |  |
|  | EPTAM | 6.0 | PPI | none | — |  |  |  |  |  | 90 |  |
|  | EPTAM | 6.0 | PPI/TM | 0.05 | PPI/TM |  |  |  |  |  | 90 |  |
|  | EPTAM | 6.0 | PPI/TM | 0.5 | PPI/TM |  |  |  |  |  | *80 |  |
|  | EPTAM | 6.0 | PPI/TM | 5.0 | PPI/TM |  |  |  |  |  | *0 |  |
|  | EPTAM | 6.0 | PPI | none | — |  |  |  |  |  | 90 |  |
|  | EPTAM | 6.0 | PPI/TM | 0.5 | PPI/TM |  |  |  |  |  | *50 |  |
|  | EPTAM | 6.0 | PPI/TM | 5.0 | PPI/TM |  |  |  |  |  | *0 |  |
| 19 | VERNAM | 1.25 | PPI | none | — | 100 | 100 | 60 | 100 | 90 |  |  |
|  | VERNAM | 1.25 | PPI | 5.0 | IF | *80 | *95 | 70 | 100 | 90 |  |  |
|  | VERNAM | 6.0 | PPI | none | — |  |  |  |  |  | 95 | 60 |
|  | VERNAM | 6.0 | PPI | 5.0 | IF |  |  |  |  |  | *60 | *40 |
|  | VERNAM | 6.0 | PPI | none | — |  |  |  |  |  |  | 55 |
|  | VERNAM | 6.0 | PPI | 1.0 | IF |  |  |  |  |  |  | 55 |
|  | VERNAM | 6.0 | PPI | 5.0 | IF |  |  |  |  |  |  | *45 |
| 20 | VERNAM | 1.25 | PPI | none | — | 100 | 100 | 60 | 100 | 90 |  |  |
|  | VERNAM | 1.25 | PPI | 5.0 | IF | 100 | 100 | 60 | *95 | 90 |  |  |
|  | VERNAM | 6.0 | PPI | none | — |  |  |  |  |  | 95 | 60 |
|  | VERNAM | 6.0 | PPI | 5.0 | IF |  |  |  |  |  | *40 | 60 |
|  | EPTAM | 5.0 | PPI | none | — |  |  |  |  |  | 85 |  |
|  | EPTAM | 5.0 | PPI/TM | 0.05 | PPI/TM |  |  |  |  |  | 85 |  |
|  | EPTAM | 5.0 | PPI/TM | 0.5 | PPI/TM |  |  |  |  |  | *35 |  |
|  | EPTAM | 5.0 | PPI/TM | 5.0 | PPI/TM |  |  |  |  |  | *15 |  |
|  | EPTAM | 6.0 | PPI | none | — |  |  |  |  |  | 90 |  |
|  | EPTAM | 6.0 | PPI/TM | 0.05 | PPI/TM |  |  |  |  |  | 90 |  |
|  | EPTAM | 6.0 | PPI/TM | 0.5 | PPI/TM |  |  |  |  |  | 90 |  |
|  | EPTAM | 6.0 | PPI/TM | 5.0 | PPI/TM |  |  |  |  |  | *30 |  |
| 21 | VERNAM | 1.25 | PPI | none | — | 80 | 75 | 60 | 85 | 65 |  |  |
|  | VERNAM | 1.25 | PPI | 5.0 | IF | 80 | 75 | 60 | *65 | *60 |  |  |
|  | VERNAM | 6.0 | PPI | none | — |  |  |  |  |  | 90 | 60 |
|  | VERNAM | 6.0 | PPI | 5.0 | IF |  |  |  |  |  | *60 | 60 |
|  | VERNAM | 1.25 | PPI | none | — |  |  |  | 50 |  |  |  |
|  | VERNAM | 1.25 | PPI | 1.0 | IF |  |  |  | 50 |  |  |  |
|  | VERNAM | 1.25 | PPI | 5.0 | IF |  |  |  | 50 |  |  |  |
|  | VERNAM | 6.0 | PPI | none | — |  |  |  |  |  |  | 25 |
|  | VERNAM | 6.0 | PPI | 1.0 | IF |  |  |  |  |  |  | *10 |
|  | VERNAM | 6.0 | PPI | 5.0 | IF |  |  |  |  |  |  | 25 |
|  | VERNAM | 6.0 | PPI | none | — |  |  |  |  |  |  | 50 |
|  | VERNAM | 6.0 | PPI/TM | 1.0 | PPI/TM |  |  |  |  |  |  | 50 |
|  | VERNAM | 6.0 | PPI/TM | 2.0 | PPI/TM |  |  |  |  |  |  | 50 |
|  | VERNAM | 6.0 | PPI/TM | 5.0 | PPI/TM |  |  |  |  |  |  | 50 |
|  | SUTAN | 6.0 | PPI | none | — |  |  |  | 40 |  |  |  |
|  | SUTAN | 6.0 | PPI/TM | 1.0 | PPI/TM |  |  |  | 40 |  |  |  |
|  | SUTAN | 6.0 | PPI/TM | 5.0 | PPI.TM |  |  |  | 40 |  |  |  |
| 22 | VERNAM | 1.25 | PPI | none | — | 90 | 100 | 70 | 100 | 75 |  |  |
|  | VERNAM | 1.25 | PPI | 5.0 | IF | *60 | 100 | 70 | 100 | 75 |  |  |
|  | VERNAM | 6.0 | PPI | none | — |  |  |  |  |  | 90 | 40 |
|  | VERNAM | 6.0 | PPI | 5.0 | IF |  |  |  |  |  | 90 | 40 |

TABLE V

| Cmpd. No. | Herbicide | Rate | Herbicide Method | Antidote Rate | Antidote Method | Water grass | Foxtail | Wild Oat | Shatter-cane | Mustard | Johnson grass |
|---|---|---|---|---|---|---|---|---|---|---|---|
| 1 | VERNAM | 1.0 | PPI | none | — | 70 | | 95 | | | |
| | VERNAM | 1.0 | PPI | 1.0 | IF | 70 | | 95 | | | |
| | VERNAM | 1.0 | PPI | 5.0 | IF | 70 | | 95 | | | |
| | VERNAM | 1.0 | PPI | none | — | 100 | | 70 | | | |
| | VERNAM | 1.0 | PPI | 1.0 | IF | 100 | | 70 | | | |
| | VERNAM | 1.0 | PPI | 5.0 | IF | 100 | | 70 | | | |
| | VERNAM | 6.0 | PPI | none | — | 100 | 100 | | | | |
| | VERNAM | 6.0 | PPI/TM | 1.0 | PPI/TM | 100 | 100 | | | | |
| | VERNAM | 6.0 | PPI/TM | 5.0 | PPI/TM | 100 | 100 | | | | |
| | VERNAM | 6.0 | PPI | none | — | 85 | 90 | | | | |
| | VERNAM | 6.0 | PPI/TM | 1.0 | PPI/TM | 85 | 90 | | | | |
| | VERNAM | 6.0 | PPI/TM | 5.0 | PPI/TM | 85 | 90 | | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| | LASSO | 3.0 | PES | none | — | 99 | | | | | |
| | LASSO | 3.0 | PES | 5.0 | IF | 99 | | | | | |
| | LASSO | 3.0 | PES | none | — | 100 | 100 | | | | |
| | LASSO | 3.0 | PES/TM | 5.0 | PES/TM | 100 | 100 | | | | |
| | LASSO | 4.0 | PES | none | — | 100 | 100 | | | | |
| | LASSO | 4.0 | PES/TM | 5.0 | PES/TM | 100 | 100 | | | | |
| 2 | VERNAM | 1.25 | PPI | none | — | 90 | | 100 | | | |
| | VERNAM | 1.25 | PPI | 1.0 | IF | 90 | | 100 | | | |
| | VERNAM | 1.25 | PPI | 5.0 | IF | 90 | | 100 | | | |
| | VERNAM | 1.25 | PPI | none | — | | 85 | 100 | | | |
| | VERNAM | 1.25 | PPI/TM | 1.0 | PPI/TM | | 85 | 100 | | | |
| | VERNAM | 1.25 | PPI/TM | 5.0 | PPI/TM | | 85 | 100 | | | |
| | LASSO | 3.5 | PES | none | — | 100 | | | | | |
| | LASSO | 3.5 | PES | 5.0 | IF | 100 | | | | | |
| | TERIDOX | 1.0 | PES | none | — | 100 | | | | | |
| | TERIDOX | 1.0 | PES | 5.0 | IF | 100 | | | | | |
| 3 | VERNAM | 1.25 | PPI | none | — | 85 | | | | | |
| | VERNAM | 1.25 | PPI | 1.0 | IF | 85 | | | | | |
| | VERNAM | 1.25 | PPI | 5.0 | IF | 85 | | | | | |
| | VERNAM | 5.0 | PPI | none | — | 100 | 100 | | | | |
| | VERNAM | 5.0 | PPI | 1.0 | IF | 100 | 100 | | | | |
| | VERNAM | 5.0 | PPI | 5.0 | IF | 100 | 100 | | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| | SUTAN | 5.0 | PPI | none | — | | | 100 | | | 100 |
| | SUTAN | 5.0 | PPI/TM | 1.0 | PPI/TM | | | 100 | | | 100 |
| | SUTAN | 5.0 | PPI/TM | 5.0 | PPI/TM | | | 100 | | | 100 |
| | LASSO | 3.0 | PES | none | — | 100 | 100 | | | | |
| | LASSO | 3.0 | PES/TM | 5.0 | PES/TM | 100 | 100 | | | | |
| | LASSO | 4.0 | PES | none | — | 100 | 100 | | | | |
| | LASSO | 4.0 | PES/TM | 5.0 | PES/TM | 100 | 100 | | | | |
| 4 | VERNAM | 1.25 | PPI | none | — | 100 | | 70 | | | |
| | VERNAM | 1.25 | PPI | 1.0 | IF | 100 | | 70 | | | |
| | VERNAM | 1.25 | PPI | 5.0 | IF | 100 | | 70 | | | |
| | VERNAM | 1.25 | PPI | none | — | 70 | | 100 | | | |
| | VERNAM | 1.25 | PPI/TM | 0.25 | PPI/TM | 70 | | 100 | | | |
| | VERNAM | 1.25 | PPI/TM | 0.5 | PPI/TM | 70 | | 100 | | | |
| | VERNAM | 1.25 | PPI/TM | 1.0 | PPI/TM | 70 | | 100 | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| | RONEET | 3.0 | PPI | none | — | 95 | | | 100 | | |
| | RONEET | 3.0 | PPI | 1.0 | IF | 95 | | | 100 | | |
| | RONEET | 3.0 | PPI | 5.0 | IF | 95 | | | 100 | | |
| | LASSO | 3.0 | PES | none | — | 99 | | | | | |
| | LASSO | 3.0 | PES | 5.0 | IF | 99 | | | | | |
| | LASSO | 3.5 | PES | none | — | 100 | | | | | |
| | LASSO | 3.5 | PES | 5.0 | IF | 100 | | | | | |
| | TERIDOX | 1.0 | PES | none | — | 100 | | | | | |
| | TERIDOX | 1.0 | PES | 5.0 | IF | 100 | | | | | |
| | ATRAZINE | 0.25 | PES | none | — | 95 | | | | 100 | |
| | ATRAZINE | 0.25 | PES | 5.0 | IF | 95 | | | | 100 | |
| 6 | VERNAM | 1.0 | PPI | none | — | 70 | | 100 | | | |
| | VERNAM | 1.0 | PPI | 1.0 | IF | 70 | | 100 | | | |
| | VERNAM | 1.0 | PPI | 5.0 | IF | 70 | | 100 | | | |
| | VERNAM | 6.0 | PPI | none | — | 100 | 90 | | | | |
| | VERNAM | 6.0 | PPI/TM | 1.0 | PPI/TM | 100 | 90 | | | | |
| | VERNAM | 6.0 | PPI/TM | 2.0 | PPI/TM | 100 | 90 | | | | |
| | VERNAM | 6.0 | PPI/TM | 5.0 | PPI/TM | 100 | 90 | | | | |
| | VERNAM | 6.0 | PPI | none | — | 100 | 100 | | | | |
| | VERNAM | 6.0 | PPI/TM | 1.0 | PPI/TM | 100 | 100 | | | | |
| | VERNAM | 6.0 | PPI/TM | 5.0 | PPI/TM | 100 | 100 | | | | |
| | VERNAM | 6.0 | PPI | none | — | 85 | 90 | | | | |
| | VERNAM | 6.0 | PPI/TM | 1.0 | PPI/TM | 85 | 90 | | | | |

TABLE V-continued

| Cmpd. No. | Herbicide | Rate | Herbicide Method | Antidote Rate | Antidote Method | Water grass | Foxtail | Wild Oat | Shatter-cane | Mustard | Johnson grass |
|---|---|---|---|---|---|---|---|---|---|---|---|
| | VERNAM | 6.0 | PPI/TM | 5.0 | PPI/TM | 85 | 90 | | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| | LASSO | 3.0 | PES | none | — | 99 | | | | | |
| | LASSO | 3.0 | PES | 5.0 | IF | 99 | | | | | |
| | ATRAZINE | 0.25 | PES | none | — | 95 | | | | | |
| | ATRAZINE | 0.25 | PES | 5.0 | IF | 95 | | | | | |
| 7 | VERNAM | 6.0 | PPI | none | — | 85 | 90 | | | | |
| | VERNAM | 6.0 | PPI/TM | 1.0 | PPI/TM | 85 | 90 | | | | |
| | VERNAM | 6.0 | PPI/TM | 5.0 | PPI/TM | 85 | 90 | | | | |
| 8 | VERNAM | 1.25 | PPI | none | — | 90 | | 100 | | | |
| | VERNAM | 1.25 | PPI | 1.0 | IF | 90 | | 100 | | | |
| | VERNAM | 1.25 | PPI | 5.0 | IF | 90 | | 100 | | | |
| | VERNAM | 6.0 | PPI | none | — | 100 | 100 | | | | |
| | VERNAM | 6.0 | PPI/TM | 1.0 | PPI/TM | 100 | 100 | | | | |
| | VERNAM | 6.0 | PPI/TM | 5.0 | PPI/TM | 100 | 100 | | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| | RONEET | 4.0 | PPI | none | — | | 80 | | 100 | | |
| | RONEET | 4.0 | PPI | 1.0 | IF | | 80 | | 100 | | |
| | RONEET | 4.0 | PPI | 5.0 | IF | | 80 | | 100 | | |
| | LASSO | 3.0 | PES | none | — | 99 | | | | | |
| | LASSO | 3.0 | PES | 5.0 | IF | 99 | | | | | |
| | LASSO | 3.5 | PES | none | — | 100 | | | | | |
| | LASSO | 3.5 | PES | 5.0 | IF | 100 | | | | | |
| | TERIDOX | 1.0 | PES | none | — | 100 | | | | | |
| | TERIDOX | 1.0 | PES | 5.0 | IF | 100 | | | | | |
| | ATRAZINE | 0.25 | PES | none | — | 95 | | | | 100 | |
| | ATRAZINE | 0.25 | PES | 5.0 | IF | 95 | | | | 100 | |
| 9 | VERNAM | 6.0 | PPI | none | — | 100 | 100 | | | | |
| | VERNAM | 6.0 | PPI/TM | 1.0 | PPI/TM | 100 | 100 | | | | |
| | VERNAM | 6.0 | PPI/TM | 5.0 | PPI/TM | 100 | 100 | | | | |
| | VERNAM | 6.0 | PPI | none | — | 85 | 90 | | | | |
| | VERNAM | 6.0 | PPI/TM | 5.0 | PPI/TM | 85 | 90 | | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| 10 | VERNAM | 5.0 | PPI | none | — | 100 | 95 | | | | |
| | VERNAM | 5.0 | PPI | 1.0 | IF | 100 | 95 | | | | |
| | VERNAM | 5.0 | PPI | 5.0 | IF | 100 | 95 | | | | |
| | EPTAM | 6.0 | PPI | none | — | | 100 | | | | 100 |
| | EPTAM | 6.0 | PPI/TM | 0.05 | PPI/TM | | 100 | | | | 100 |
| | EPTAM | 6.0 | PPI/TM | 0.5 | PPI/TM | | 100 | | | | 100 |
| | EPTAM | 6.0 | PPI/TM | 5.0 | PPI/TM | | 100 | | | | 100 |
| | EPTAM | 6.0 | PPI | none | — | 100 | 100 | | | | |
| | EPTAM | 6.0 | PPI/TM | 0.5 | PPI/TM | 100 | 100 | | | | |
| | EPTAM | 6.0 | PPI/TM | 5.0 | PPI/TM | 100 | 100 | | | | |
| | RONEET | 4.0 | PPI | none | — | | 80 | | 100 | | |
| | RONEET | 4.0 | PPI | 1.0 | IF | | 80 | | 100 | | |
| | RONEET | 4.0 | PPI | 5.0 | IF | | 80 | | 100 | | |
| 11 | EPTAM | 6.0 | PPI | none | — | | 100 | | | | 100 |
| | EPTAM | 6.0 | PPI/TM | 0.05 | PPI/TM | | 100 | | | | 100 |
| | EPTAM | 6.0 | PPI/TM | 0.5 | PPI/TM | | 100 | | | | 100 |
| | EPTAM | 6.0 | PPI/TM | 5.0 | PPI/TM | | 100 | | | | 100 |
| | EPTAM | 6.0 | PPI | none | — | 100 | 100 | | | | |
| | EPTAM | 6.0 | PPI/TM | 0.5 | PPI/TM | 100 | 100 | | | | |
| | EPTAM | 6.0 | PPI/TM | 5.0 | PPI/TM | 100 | 100 | | | | |
| | RONEET | 4.0 | PPI | none | — | | 80 | | 100 | | |
| | RONEET | 4.0 | PPI | — | — | | 80 | | 100 | | |
| | RONEET | 4.0 | PPI | — | — | | 80 | | 100 | | |
| 12 | EPTAM | 6.0 | PPI | none | — | | 100 | | | | 100 |
| | EPTAM | 6.0 | PPI/TM | 0.05 | PPI/TM | | 100 | | | | 100 |
| | EPTAM | 6.0 | PPI/TM | 0.5 | PPI/TM | | 100 | | | | 100 |
| | EPTAM | 6.0 | PPI/TM | 5.0 | PPI/TM | | 100 | | | | 100 |
| | EPTAM | 6.0 | PPI | none | — | 100 | 100 | | | | |
| | EPTAM | 6.0 | PPI/TM | 0.5 | PPI/TM | 100 | 100 | | | | |
| | EPTAM | 6.0 | PPI/TM | 5.0 | PPI/TM | 100 | 100 | | | | |
| | EPTAM | 6.0 | PPI | none | — | 100 | 100 | | | | |
| | EPTAM | 6.0 | PPI | 0.5 | PPI | 100 | 100 | | | | |
| | EPTAM | 6.0 | PPI | 5.0 | PPI | 100 | 100 | | | | |
| 15 | VERNAM | 1.25 | PPI | none | — | 90 | 70 | | | | |
| | VERNAM | 1.25 | PPI | 1.0 | IF | 90 | 70 | | | | |
| | VERNAM | 1.25 | PPI | 5.0 | IF | 90 | 50 | | | | |
| 16 | EPTAM | 5.0 | PPI | none | — | 98 | | | | | 98 |
| | EPTAM | 5.0 | PPI/TM | 0.05 | PPI/TM | 98 | | | | | 98 |
| | EPTAM | 5.0 | PPI/TM | 0.5 | PPI/TM | 98 | | | | | 98 |
| | EPTAM | 5.0 | PPI/TM | 5.0 | PPI/TM | 98 | | | | | 98 |
| 18 | VERNAM | 1.0 | PPI | none | — | 97 | 85 | | | | |

TABLE V-continued

| Cmpd. No. | Herbicide | Rate | Herbicide Method | Antidote Rate | Antidote Method | Water grass | Foxtail | Wild Oat | Shatter-cane | Mustard | Johnson grass |
|---|---|---|---|---|---|---|---|---|---|---|---|
| | VERNAM | 1.0 | PPI | 1.0 | IF | 97 | 85 | | | | |
| | VERNAM | 1.0 | PPI | 5.0 | IF | 97 | 85 | | | | |
| | VERNAM | 1.25 | PPI | none | — | 90 | 85 | | | | |
| | VERNAM | 1.25 | PPI | 1.0 | IF | 90 | 85 | | | | |
| | VERNAM | 1.25 | PPI | 5.0 | IF | 90 | 85 | | | | |
| | EPTAM | 6.0 | PPI | none | — | | 100 | | | | 100 |
| | EPTAM | 6.0 | PPI/TM | 0.05 | PPI/TM | | 100 | | | | 100 |
| | EPTAM | 6.0 | PPI/TM | 0.5 | PPI/TM | | 100 | | | | 100 |
| | EPTAM | 6.0 | PPI/TM | 5.0 | PPI/TM | | 100 | | | | 100 |
| | EPTAM | 6.0 | PPI | none | — | 100 | 100 | | | | |
| | EPTAM | 6.0 | PPI/TM | 0.5 | PPI/TM | 100 | 100 | | | | |
| | EPTAM | 6.0 | PPI/TM | 5.0 | PPI/TM | 100 | 100 | | | | |
| 19 | VERNAM | 6.0 | PPI | none | — | 100 | 100 | | | | |
| | VERNAM | 6.0 | PPI | 1.0 | IF | 100 | 100 | | | | |
| | VERNAM | 6.0 | PPI | 5.0 | IF | 100 | 100 | | | | |
| 20 | EPTAM | 5.0 | PPI | none | — | 98 | | | | | 98 |
| | EPTAM | 5.0 | PPI/TM | 0.05 | PPI/TM | 98 | | | | | 98 |
| | EPTAM | 5.0 | PPI/TM | 0.5 | PPI/TM | 98 | | | | | 98 |
| | EPTAM | 5.0 | PPI/TM | 5.0 | PPI/TM | 98 | | | | | 98 |
| | EPTAM | 6.0 | PPI | none | — | | 100 | | | | 100 |
| | EPTAM | 6.0 | PPI/TM | 0.05 | PPI/TM | | 100 | | | | 100 |
| | EPTAM | 6.0 | PPI/TM | 0.5 | PPI/TM | | 100 | | | | 100 |
| | EPTAM | 6.0 | PPI/TM | 5.0 | PPI/TM | | 100 | | | | 100 |
| 21 | VERNAM | 1.25 | PPI | none | — | 95 | 80 | | | | |
| | VERNAM | 1.25 | PPI | 1.0 | IF | 95 | 80 | | | | |
| | VERNAM | 1.25 | PPI | 5.0 | IF | 95 | 80 | | | | |
| | VERNAM | 6.0 | PPI | none | — | 95 | 95 | | | | |
| | VERNAM | 6.0 | PPI | 1.0 | IF | 95 | 95 | | | | |
| | VERNAM | 6.0 | PPI | 5.0 | IF | 95 | 80 | | | | |
| | VERNAM | 6.0 | PPI | none | — | 100 | 97 | | | | |
| | VERNAM | 6.0 | PPI/TM | 1.0 | PPI/TM | 100 | 97 | | | | |
| | VERNAM | 6.0 | PPI/TM | 2.0 | PPI/TM | 100 | 97 | | | | |
| | VERNAM | 6.0 | PPI/TM | 5.0 | PPI/TM | 100 | 97 | | | | |
| | SUTAN | 6.0 | PPI | none | — | 95 | 99 | | | | |
| | SUTAN | 6.0 | PPI/TM | 1.0 | PPI/TM | 95 | 99 | | | | |
| | SUTAN | 6.0 | PPI/TM | 5.0 | PPI/TM | 95 | 99 | | | | |

Test Results

The compounds of this invention show good antidotal activity for a variety of crops. The composition of thiocarbamate herbicide and antidote compound was particularly effective for the reduction of herbicidal injury to corn crops. Use of the antidote compounds did not result in a reduction of herbicidal injury to weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulations are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applied by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. A compound having the formula

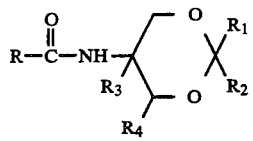

in which

R is haloalkyl wherein halo is chlorine, bromine or iodine and the alkyl group has 1–4 carbon atoms, inclusive;

$R_1$ is selected from the group consisting of hydrogen; lower alkyl having 1–4 carbon atoms, inclusive; alkenyl having 2–4 carbon atoms, inclusive; and phenyl;

$R_2$ is selected from the group consisting of hydrogen and lower alkyl having 1–4 carbon atoms, inclusive;

$R_3$ is selected from the group consisting of hydrogen and lower alkyl having 1–4 carbon atoms, inclusive;

$R_4$ is selected from the group consisting of hydrogen and a nitro group; and either $R_3$ is hydrogen or $R_4$ is hydrogen.

2. A compound as defined in claim 1 wherein R is dibromoethyl, $R_1$ is hydrogen, $R_2$ is hydrogen, $R_3$ is methyl and $R_4$ is hydrogen.

3. A compound as defined in claim 1 wherein R is dibromoethyl, $R_1$ is methyl, $R_2$ is hydrogen, $R_3$ is methyl and $R_4$ is hydrogen.

4. A compound as defined in claim 1 wherein R is dibromoethyl, $R_1$ is hydrogen, $R_2$ is hydrogen, $R_3$ is ethyl and $R_4$ is hydrogen.

5. A compound as defined in claim 1 wherein R is dibromoethyl, $R_1$ is hydrogen, $R_2$ is hydrogen, $R_3$ is ethyl and $R_4$ is hydrogen.

6. A compound as defined in claim 1 wherein R is dichloromethyl, $R_1$ is methyl, $R_2$ is ethyl, $R_3$ is methyl and $R_4$ is hydrogen.

7. A compound as defined in claim 1 wherein R is chloromethyl, $R_1$ is hydrogen, $R_2$ is hydrogen, $R_3$ is methyl and $R_4$ is hydrogen.

8. A compound as defined in claim 1 wherein R is chloromethyl, $R_1$ is hydrogen, $R_2$ is hydrogen, $R_3$ is methyl and $R_4$ is hydrogen.

9. A compound as defined in claim 1 wherein R is chloromethyl, $R_1$ is methyl, $R_2$ is hydrogen, $R_3$ is methyl and $R_4$ is hydrogen.

10. A compound as defined in claim 1 wherein R is dichloromethyl, $R_1$ is methyl, $R_2$ is hydrogen, $R_3$ is methyl and $R_4$ is hydrogen.

11. A compound as defined in claim 1 wherein R is chloromethyl, $R_1$ is hydrogen, $R_2$ is hydrogen, $R_3$ is ethyl and $R_4$ is hydrogen.

12. A compound as defined in claim 1 wherein R is dichloromethyl, $R_1$ is hydrogen, $R_2$ is hydrogen, $R_3$ is ethyl and $R_4$ is hydrogen.

13. A compound as defined in claim 1 wherein R is chloromethyl, $R_1$ is methyl, $R_2$ is methyl, $R_3$ is methyl and $R_4$ is hydrogen.

14. A compound as defined in claim 1 wherein R is dichloromethyl, $R_1$ is methyl, $R_2$ is methyl, $R_3$ is methyl and $R_4$ is hydrogen.

15. A compound as defined in claim 1 wherein R is chloromethyl, $R_1$ is methyl, $R_2$ is methyl, $R_3$ is ethyl and $R_4$ is hydrogen.

16. A compound as defined in claim 1 wherein R is chloromethyl, $R_1$ is ethyl, $R_2$ is methyl, $R_3$ is methyl and $R_4$ is hydrogen.

17. A compound as defined in claim 1 wherein R is chloromethyl, $R_1$ is allyl, $R_2$ is hydrogen, $R_3$ is methyl and $R_4$ is hydrogen.

18. A compound as defined in claim 1 wherein R is dichloromethyl, $R_1$ is allyl, $R_2$ is hydrogen, $R_3$ is methyl and $R_4$ is hydrogen.

19. A compound as defined in claim 1 wherein R is chloromethyl, $R_1$ is phenyl, $R_2$ is hydrogen, $R_3$ is methyl and $R_4$ is hydrogen.

20. A compound as defined in claim 1 wherein R is dichloromethyl, $R_1$ is phenyl, $R_2$ is hydrogen, $R_3$ is methyl and $R_4$ is hydrogen.

21. A composition comprising (a) an herbicidally effective amount of a thiocarbamate compound of the formula

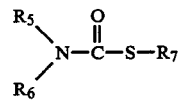

in which $R_5$ is alkyl having 1–6 carbon atoms, inclusive;

$R_6$ is selected from the group consisting of alkyl having 1–6 carbon atoms, inclusive; and cyclohexyl; or $R_5$ and $R_6$ form indistinguishable parts of a single alkylene ring having 4–10 carbon atoms, inclusive; and $R_7$ is selected from the group consisting of alkyl having 1–6 carbon atoms, inclusive; haloalkyl wherein halo is selected from the group consisting of chlorine, bromine and iodine and alkyl has 1–6 carbon atoms, inclusive; alkenyl having 2–6 carbon atoms, inclusive; halo alkenyl wherein halo is selected from the group consisting of chlorine, bromine and iodine and alkenyl has 2–6 carbon atoms, inclusive; benzyl; and halo-substituted benzyl, wherein halo is selected from the group consisting of chlorine,, bromine and iodine; and (b) a non-phytotoxic antidotally effective amount of a compound of the formula

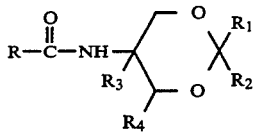

in which

R is haloalkyl wherein halo is chlorine, bromine or iodine and the alkyl group has 1–4 carbon atoms, inclusive;

$R_1$ is selected from the group consisting of hydrogen; lower alkyl having 1–4 carbon atoms, inclusive; alkenyl having 2–4 carbon atoms, inclusive; and phenyl;

$R_2$ is selected from the group consisting of hydrogen and lower alkyl having 1–4 carbon atoms, inclusive;

$R_3$ is selected from the group consisting of hydrogen and lower alkyl having 1–4 carbon atoms, inclusive;

$R_4$ is selected from the group consisting of hydrogen and a nitro group; and either $R_3$ is hydrogen or $R_4$ is hydrogen.

22. A composition as defined in claim 21 wherein R is dibromoethyl, $R_1$ is hydrogen, $R_2$ is hydrogen, $R_3$ is methyl and $R_4$ is hydrogen.

23. A composition as defined in claim 21 wherein R is dibromoethyl, $R_1$ is methyl, $R_2$ is hydrogen, $R_3$ is methyl and $R_4$ is hydrogen.

24. A composition as defined in claim 21 wherein R is dibromoethyl, $R_1$ is hydrogen, $R_2$ is hydrogen, $R_3$ is ethyl and $R_4$ is hydrogen.

25. A composition as defined in claim 21 wherein R is dichloromethyl, $R_1$ is methyl, $R_2$ is ethyl, $R_3$ is methyl and $R_4$ is hydrogen.

26. A composition as defined in claim 21 wherein R is chloromethyl, $R_1$ is hydrogen, $R_2$ is hydrogen, $R_3$ is methyl and $R_4$ is hydrogen.

27. A composition as defined in claim 21 wherein R is chloromethyl, $R_1$ is methyl, $R_2$ is hydrogen, $R_3$ is methyl and $R_4$ is hydrogen.

28. A composition as defined in claim 21 wherein R is dichloromethyl, $R_1$ is methyl, $R_2$ is hydrogen, $R_3$ is methyl and $R_4$ is hydrogen.

29. A composition as defined in claim 21 wherein R is chloromethyl, $R_1$ is hydrogen, $R_2$ is hydrogen, $R_3$ is ethyl and $R_4$ is hydrogen.

30. A composition as defined in claim 21 wherein R is dichloromethyl, $R_1$ is hydrogen, $R_2$ is hydrogen, $R_3$ is ethyl and $R_4$ is hydrogen.

31. A composition as defined in claim 21 wherein R is chloromethyl, $R_1$ is methyl, $R_2$ is methyl, $R_3$ is methyl and $R_4$ is hydrogen.

32. A composition as defined in claim 21 wherein R is dichlormethyl, $R_1$ is methyl, $R_2$ is methyl, $R_3$ is methyl and $R_4$ is hydrogen.

33. A composition as defined in claim 21 wherein R is chloromethyl, $R_1$ is methyl, $R_2$ is methyl, $R_3$ is ethyl and $R_4$ is hydrogen.

34. A composition as defined in claim 21 wherein R is dichloromethyl, $R_1$ is methyl, $R_2$ is methyl, $R_3$ is methyl and $R_4$ is hydrogen.

35. A composition as defined in claim 21 wherein R is chloromethyl, $R_1$ is ethyl, $R_2$ is methyl, $R_3$ is methyl and $R_4$ is hydrogen.

36. A composition as defined in claim 21 wherein R is chloromethyl, $R_1$ is allyl, $R_2$ is hydrogen, $R_3$ is methyl and $R_4$ is hydrogen.

37. A composition as defined in claim 21 wherein R is dichloromethyl, $R_1$ is allyl, $R_2$ is hydrogen, $R_3$ is methyl and $R_4$ is hydrogen.

38. A composition as defined in claim 21 wherein R is chloromethyl, $R_1$ is phenyl, $R_2$ is hydrogen, $R_3$ is methyl and $R_4$ is hydrogen.

39. A composition as defined in claim 21 wherein R is dichloromethyl, $R_1$ is phenyl, $R_2$ is hydrogen, $R_3$ is methyl and $R_4$ is hydrogen.

40. A composition as defined in claim 21 wherein R is dichloromethyl, $R_1$ is methyl, $R_2$ is methyl, $R_3$ is hydrogen and $R_4$ is nitrophenyl.

41. A composition as defined in claim 21 wherein R is dichloromethyl, $R_1$ is methyl, $R_2$ is hydrogen, $R_3$ is hydrogen and $R_4$ is nitrophenyl.

* * * * *